United States Patent

Lantzsch

[11] 4,215,050
[45] Jul. 29, 1980

[54] PREPARATION OF HALOGENOVINYL-γ-BUTYROLACTONES

[75] Inventor: Reinhard Lantzsch, Cologne, Fed. Rep. of Germany

[73] Assignee: Bayer Aktiengesellschaft, Leverkusen, Fed. Rep. of Germany

[21] Appl. No.: 949,356

[22] Filed: Oct. 6, 1978

[30] Foreign Application Priority Data

Oct. 26, 1977 [DE] Fed. Rep. of Germany ....... 2747824

[51] Int. Cl.² ........................................... C07D 307/32
[52] U.S. Cl. ................................. 260/343.6; 560/125; 560/178; 568/848
[58] Field of Search ...................................... 260/343.6

[56] References Cited

U.S. PATENT DOCUMENTS

| | | | |
|---|---|---|---|
| 2,386,749 | 10/1945 | Ruzicka | 260/343.6 |
| 4,102,896 | 7/1978 | Raphael | 260/343.6 |
| 4,138,584 | 2/1979 | Klemmensen et al. | 260/343.6 X |

FOREIGN PATENT DOCUMENTS

| | | | |
|---|---|---|---|
| 546573 | 9/1957 | Canada | 260/343.6 |
| 2702222 | 8/1977 | Fed. Rep. of Germany | 260/343.6 |

*Primary Examiner*—Ethel G. Love
*Attorney, Agent, or Firm*—Sprung, Felfe, Horn, Lynch & Kramer

[57] ABSTRACT

Halogenovinyl-γ-butyralactones, used as intermediates in the preparation of insecticidally active cyclopropanecarboxylic acid esters, and of the formula

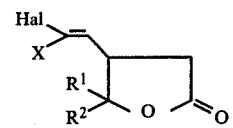

in which
Hal represents F, Cl or Br,
X represents H, F, Cl or Br and
$R^1$ and $R^2$, which may be identical or different, each represents $C_{1-4}$-alkyl or $R^1$ and $R^2$, together with the adjacent C atom, form a cycloaliphatic ring with up to 7 C atoms, are produced by basic de-acetylation of the novel corresponding α-acetyl compounds. Syntheses are given for preparing the acetyl compounds, including novel intermediates of the formulas

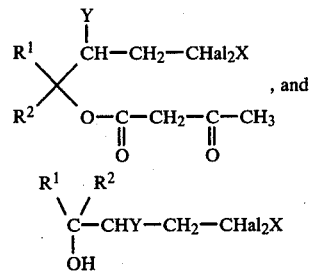

14 Claims, No Drawings

PREPARATION OF HALOGENOVINYL-γ-BUTYROLACTONES

The present invention relates to an unobvious process for the preparation of certain halogenovinyl-γ-butyrolactones, some of which are known, to certain new halogenovinyl-γ-butyrolactones and to intermediates for their preparation.

Vinyl-substituted γ-butyrolactones and processes for their preparation have already been disclosed (see DT-OS (German Published Specification) Nos. 2 461 525 and 2 509 576). However, the processes described therein are not very economical and furthermore are restricted to vinyl-substituted and dialkylvinyl-substituted γ-butyrolactones.

It has also been disclosed that 4-methyl-3-(2',2'-dichlorovinyl)-γ-valerolactone is formed as a by-product during the saponification of 2,2-dimethyl-3-(2',2'-dichlorovinyl)-cyclopropane-1-carboxylic acid (see Pestic. Sic. 1974 (5) pages 792 to 793).

A process for the preparation of 2,2-disubstituted vinyl-γ-butyrolactones has also been disclosed (see DT-OS (German Published Specification) No. 2 702 222), in which, however, many stages are needed to prepare the starting compound required, and which is too expensive for a preparation on an industrial scale since, for example, relatively large amounts of aluminum salts and zinc salts are obtained.

The present invention now provides:

(1) a process for the preparation of a halogenovinyl-γ-butyrolactone of the general formula

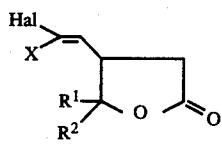

in which
Hal represents F, Cl or Br,
X represents H, F, Cl or Br and
$R^1$ and $R^2$, which may be identical or different, each represent $C_{1-4}$-alkyl or $R^1$ and $R^2$, together with the adjacent C atom, form a cycloaliphatic ring with up to 7 C atoms,
in which a compound of the general formula

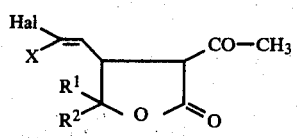

in which Hal, X, $R^1$ and $R^2$ have the meanings stated above, is deacetylated;

(2) as new compounds, the halogenovinyl-γ-butyrolactones of the general formula (I), in which Hal, X, $R^1$ and $R^2$ have the meaning stated above, but with the proviso that if Hal and X represent Cl, then $R^1$ must not represent methyl;

(3) the compounds of the general formula (II), in which Hal, X, $R^1$ and $R^2$ have the meanings stated under (1) above;

(4) a process for the preparation of a compound of the general formula (II), in which Hal, X, $R^1$ and $R^2$ have the meanings stated under (1) above, in which two mols of hydrogen halide are split off from a compound of the general formula

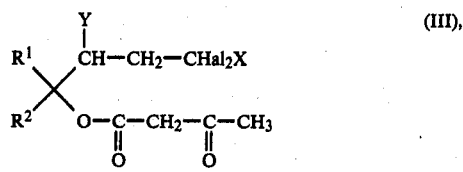

in which
Hal, X, $R^1$ and $R^2$ have the meanings stated under (1) above, but with the restriction that if X represents H or F, then only one of the radicals Hal represents fluorine, and
Y represents chlorine or bromine,
in the presence of a base and optionally in the presence of a diluent;

(5) the compounds of the general formula (III), in which Hal X, Y, $R^1$ and $R^2$ have the meanings stated under (1) above;

(6) a process for the preparation of a compound of the general formula (III), in which Hal, X, Y, $R^1$ and $R^2$ have the meanings stated under (1) above, in which (a) an alcohol of the general formula

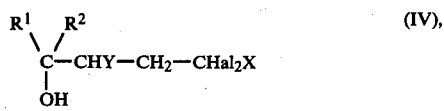

in which Hal, X, Y, $R^1$ and $R^2$ have the meanings stated above, is reacted with diketene, optionally in the presence of a diluent and in the presence of a catalyst, or (b) a compound of the general formula

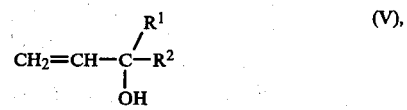

in which $R^1$ and $R^2$ have the meanings stated under (1) above, is reacted with diketene, optionally in the presence of a diluent and in the presence of a catalyst, and the resulting compound of the general formula

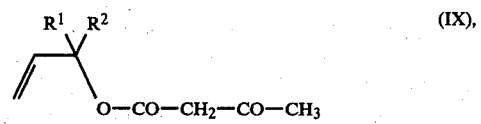

in which $R^1$ and $R^2$ have the meanings stated under (1) above, is then reacted with a compound of the general formula

in which X, Hal and Y have the meanings stated above;

(7) the compounds of the general formula (IV), in which Hal, X, Y, $R^1$ and $R^2$ have the meanings stated under (4) above; and (8) a process for the preparation of a new compound of the general formula (IV), in which a compound of the general formula

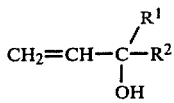

in which $R^1$ and $R^2$ have the meanings stated under (1) above, is reacted with a compound of the general formula

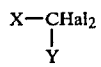

in which X, Y and Hal have the meanings stated above, with the proviso that the molecule of the formula (VI) may not contain more than two fluorine atoms, and with the proviso that if X represents H, the molecule of the formula (VI) may contain only one fluorine atom.

The process defined under (1) above makes possible an economical preparation of the halogenovinyl-γ-butyrolactones by a deacetylation reaction, in particular by a haloform reaction, starting from the new compounds (II).

If 2-acetyl-4-methyl-3-(2',2'-dichlorovinyl)-γ-valerolactone is used as the starting material in process (1), the course of the reaction can be represented by the following equation:

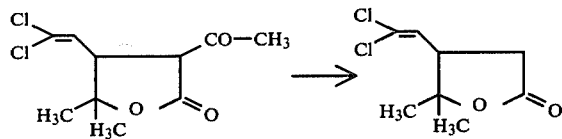

The starting materials which can be used in process (1) are defined by the general formula (II). In this formula, $R^1$ and $R^2$ preferably represent methyl. The compounds of the formula (II) are new and their preparation is described further below. Process (1) is carried out by oxidizing compounds of the general formula (II). Hypochlorite or hypobromite in aqueous solution, for example sodium hypochlorite, potassium hypochlorite, calcium hypochlorite, sodium hypobromite, potassium hypobromite or calcium hypobromite, is preferably used as the oxidizing agent. The reaction can also be carried out by introducing a halogen, for example chlorine or bromine, into an aqueous alkali metal hydroxide or alkaline earth metal hydroxide for example sodium hydroxide solution, potassium hydroxide solution or calcium hydroxide solution, and reacting this solution with the compounds of the general formula (II).

In general, process (1) is carried out at from −20° to +100° C., optionally in the presence of a diluent. Possible diluents are alcohols, such as methanol or ethanol, and ethers, such as dioxane or tetrahydrofuran. Working up is carried out by acidifying the reaction mixture, since lactones usually exist in the open-chain form in an alkaline medium. After the acidification, for example with hydrochloric acid or sulphuric acid, the diluent, if such has been employed, is distilled off and the compound of the general formula (I) is isolated in the customary manner by filtration or extraction. If necessary, they can be purified by distillation or sublimation.

The following lactones are preferably prepared by process (1): 4-methyl-3-(2',2'-dichlorovinyl)-γ-valerolactone, 4-ethyl-3-(2',2'-dichlorovinyl)-γ-valerolactone, 4,4-diethyl-3-(2',2'-dichlorovinyl)-γ-butyrolactone, 4-methyl-3-(2',2'-dibromovinyl)-γ-valerolactone, 4-ethyl-3-(2',2'-dibromovinyl)-γ-valerolactone, 4,4-diethyl-3-(2',2'-dibromovinyl)-γ-butyrolactone, 4-methyl-3-(2'-chloro-2'-bromo)-γ-valerolactone, 4-methyl-3-(2'-fluoro-2'-bromo)-γ-valerolactone, 4-methyl-3-(2'-chlorovinyl)-γ-valerolactone and 3-methyl-3-(2'-bromovinyl)-γ-valerolactone.

The compounds of the general formula (II) are new. They are obtained by the process defined under (4) above, by treating 1 mole of an acetoacetic acid ester of the general formula (III) with at least 2 mols of a base.

However, it is also possible to carry out process (4) in two stages. In this case, new compounds of the general formula

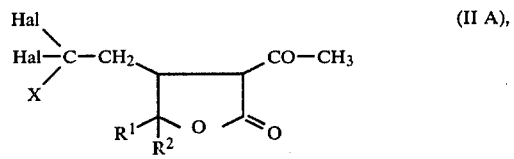

in which Hal, X, $R^1$ and $R^2$ have the meanings indicated under (4) will be obtained, which are then converted into the compounds of the general formula (II) by further treatment with bases.

If 2-methyl-3,5,5,5-tetrabromopentan-2-ol acetoacetate is used as the starting material in process (4), the course of the reaction can be represented by the following equation:

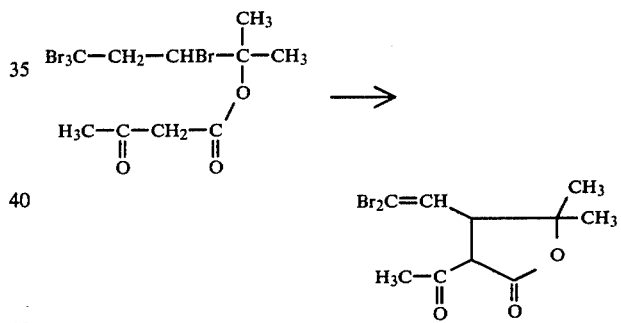

Compounds of the formula (III) are preferably used in which $R^1$ and $R^2$ represent methyl or ethyl, X represents hydrogen, fluorine, chlorine or bromine, Y represents chlorine or bromine and Hal represents fluorine, chlorine or bromine.

However, the following compounds of the formula (III) are particularly preferred: 2-methyl-3,5,5,5-tetrachloropentyl-2-acetoacetate, 2-methyl-3,5,5,5-tetrabromopentyl-2-acetoacetate, 2-methyl-5-fluoro-3,5,5-trichloropentyl-2-acetoacetate, 2-methyl-5-fluoro-3,5,5-tribromopentyl-2-acetoacetate, 2-methyl-5,5-difluoro-3,5-dibromo pentyl-2-acetoacetate, 2-methyl-3,5,5-trichloro-pentyl-2-acetoacetate, 2-methyl-3,5,5-tribromo-pentan-2-acetoacetate, 3-methyl-4,6,6,6-tetrachloro-hexyl-3-acetoacetate, 3-methyl-4,6,6,6-tetrabromo-hexyl-3-acetoacetate, 3-methyl-6-fluoro-4,6,6-trichloro-hexyl-3-acetoacetate, 3-methyl-6,6-difluoro-4,6-dibromo-hexyl-3-acetoacetate, 3-methyl-4,6,6-trichloro-hexyl-3-acetoacetate and 3-methyl-4,6,6-tribromo-hexyl-3-acetoacetate.

Possible bases are: alkali metal and alkaline earth metal hydroxides, such as sodium hydroxide, potassium hydroxide and calcium hydroxide; alcoholates, such as sodium methylate, sodium ethylate or potassium tert.-butylate; and amides, such as sodium amide.

In general, the reaction is carried out in the presence of a solvent. Possible solvents in the case of the alkali metal hydroxides are, in particular, water or alcohols, for example methanol, ethanol or glycol, or glycol monomethyl ether or monoethyl ether. If water is used as the solvent, the reaction is preferably carried out in a two-phase system using an inert organic solvent and in the presence of a catalyst. Examples of possible inert organic solvents are hydrocarbons, such as benzene, toluene, hexane an cyclohexane, and chlorohydrocarbons, such as methylene chloride and chlorobenzene.

Suitable catalysts which may be used are compounds of the general formula

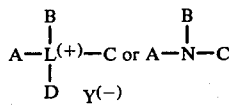

(VII)    (VIII)

in which

L represents nitrogen or phosphorus,

A, B, C and D, independently of one another, each represent optionally substituted alkyl, aralkyl or aryl, or two adjacent radicals from A, B, C and D, together with the central atom L and optionally one or more further heteroatoms, form a heterocyclic ring, and Y represents a halide, bisulphate or hydroxyl ion.

Catalyst of the general formula (VIII) are known and can be prepared by known processes (see Houben-Weyl, volume XI, 2, page 587 et seq., Georg-Thieme-Verlag, Stuttgart 1958).

Catalysts of the general formula (VII) in which A, B, C and D each represent alkyl with 1-18 C atoms, in particular methyl, ethyl, propyl, butyl, hexyl, dodecyl or octadecyl, or benzyl which is optionally substituted by $C_1$-$C_4$-alkyl, alkoxy or halogen, are preferred.

Catalysts of the general formula (VIII), in which A, B and C each represent alkyl with 1-18 C atoms, in particular methyl, ethyl, propyl, butyl, hexyl, dodecyl or octadecyl, or benzyl, are also preferred.

Particularly preferred representatives of the catalysts to be used in process (4) are: tetraethylammonium chloride, tetrabutylammonium chloride, tetrabutylammonium bromide, tetrabutylphosphonium chloride, benzyltriethylammonium chloride, benzyltributylammonium chloride, methyltrioctylammonium chloride, triethylamine, tripropylamine, tributylamine, trihexylamine and benzyldimethylamine.

The amount of catalyst can vary within wide limits. In general, about 0.1 to 10% by weight, preferably about 0.3 to 6% by weight, relative to the weight of the compound of the general formula (III) employed, have proved suitable.

If alcoholates are used as the bases in process (4), either the corresponding alcohol or other solvents such as ethers, for example diethyl ether, dioxane and tetrahydrofuran, or hydrocarbons, such as toluene, are generally used.

The first hydrogen halide molecule can usually be already split off under very mild conditions, at about −20° to +50° C., while somewhat more energetic conditions, usually about +30° C. to 120° C., are necessary for splitting off the second hydrogen halide. Reaction temperatures of about 0° to 100° C. are thus preferred.

The compounds of the general formula (III) are new. They can be prepared by the process defined under (6) above.

If 2-methyl-3,5,5,5-tetrachloropentan-2-ol and diketene are used as starting materials in process (6), the course of the reaction can be represented by the following equation:

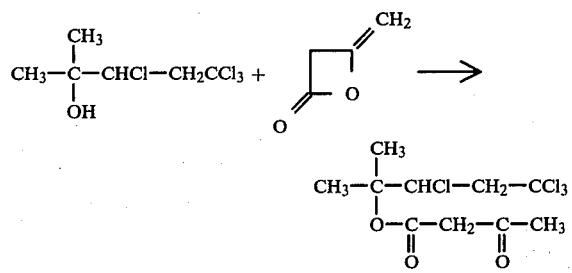

Compounds of the formula (IV) are preferably used in which $R^1$ and $R^2$ represent methyl or ethyl, Hal represents fluorine, chlorine or bromine, X represents hydrogen, fluorine, chlorine or bromine and Y represents chlorine or bromine.

However, the following compounds of the formula (IV) are particularly preferred: 2-methyl-3,5,5,5-tetrachloropentan-2-ol; 2-methyl-3,5,5,5-tetrabromo-pentan-2-ol; 2-methyl-5-fluoro-3,5,5-trichloro-pentan-2-ol; 2-methyl-5-fluoro-3,5,5-tribromo-pentan-2-ol; 2-methyl-5,5-difluoro-3,5-dibromo-pentan-2-ol; 2-methyl-3,5,5-trichloro-pentan-2-ol; 2-methyl-3,5,5-tribromo-pentan-2-ol; 3-methyl-4,6,6,6-tetrachlorohexan-3-ol; 3-methyl-4,6,6,6-tetrabromohexan-3-ol; 3-methyl-6-fluoro-4,6,6-trichloro-hexan-3-ol; 3-methyl-6,6-difluoro-4,6-dibromo-hexan-3-ol; 3-methyl-4,6,6-trichlorohexan-3-ol and 3-methyl-4,6,6-tribromo-hexan-3-ol.

Process (6) may be carried out by reacting 1 mol of a compound of the general formula (IV) with one mol of diketene, optionally in the presence of a diluent and of a catalyst. Preferably, a slight excess of diketene is used and a diluent is dispensed with. If the reaction is carried out on a relatively large scale, a diluent can nevertheless be advantageous, in order to keep the exothermic reaction under control. Possible diluents are all the organic solvents which do not react with diketene, for example hydrocarbons, such as toluene, xylene and cyclohexane, halogenohydrocarbons, such as chlorobenzene and dichlorobenzene, or ethers, such as diisopropyl ether and ethylene glycol dimethyl ether.

Suitable catalysts for process (6) which may be mentioned are, in particular, compounds of the general formula (VIII) (see above). The amount of catalyst can vary within wide limits. In general, about 0.1 to 10% by weight, preferably about 0.3 to 6% by weight, relative to the weight of the compound of the general formula (IV) employed, have proved suitable. The reaction temperature is from about 0° C. to the boiling point of diketene, preferably about 25° to 130° C. It has proved appropriate initially to introduce the compound of the general formula (IV) and the catalyst at somewhat elevated temperature and then to add the diketene dropwise. After cooling the mixture, excess diketene and diluent, if such is used, are distilled off and the residue is used for process (4).

The compounds of the general formula (II) can also be obtained by reacting the compounds of the general formula (V) with diketene, as described above, and reacting the resulting compound of the formula

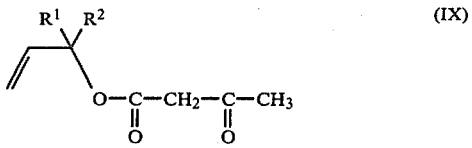

with compounds of the general formula (VI). The reaction is carried out as described for process (8) (see below). Compounds of the formula (V) in which the radicals $R^1$ and $R^2$ have the following meaning are preferably employed here: $C_{1-4}$-alkyl, or form, together with the adjacent C atom, a cycloaliphatic ring with up to 7 C atoms.

The following compounds of the formula (V) are particularly preferred: isoprene alcohol (3-methyl-1-buten-3-ol); 3-methyl-1-penten-3-ol, 1-vinyl-cyclopentan-1-ol and 1-vinyl-cyclohexan-1-ol.

Compounds of the formula (VI) are preferably employed in which X represents hydrogen, fluorine, chlorine or bromine, Y represents chlorine or bromine, and Hal represents fluorine, chlorine or bromine, and the compound of the formula (VI) should contain a maximum of 2 fluorine atoms and, in the case where X represents hydrogen, the compound of the formula (VI) should contain only one fluorine atom.

The following compounds of the formula (VI) are particularly preferred: $CCl_4$, $CBr_4$, $CCl_3Br$, $CF_2Br_2$, $CFBr_3$, $CClBr_3$, $CCl_3F$, $CHCl_3$, $CHBr_3$ and $CHFCl_2$.

Some of the compounds of the general formula (IV) are known. New and known compounds can be prepared by the process defined under (8) above.

If 3-methyl-1-buten-3-ol and carbon tetrachloride are used as the starting materials in process (8), the course of the reaction can be represented by the following equation:

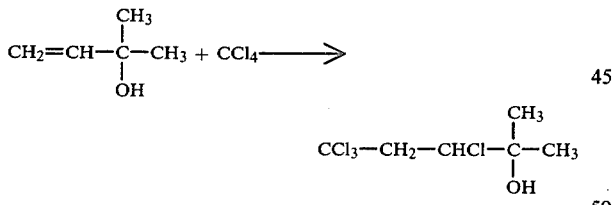

The starting materials which can be used in process (8) are defined by the general formulae (V) and (VI). They are known. The following compounds of the general formula (V) are preferably employed: isoprene-alcohol (3-methyl-1-buten-3-ol). 3-methyl-1-penten-3-ol, 3-ethyl-1-penten-3-ol, 1-vinyl-cyclopentan-1-ol and 1-vinyl-cyclohexan-1-ol.

The following compounds of the general formula (VI) are preferably employed: $CCl_4$, $CBr_4$, $CCl_3Br$, $CF_2Br_2$, $CFBr_3$, $CClBr_3$, $CCl_3F$, $CHCl_3$, $CHBr_3$ and $CHFCl_2$.

The reaction can be carried out in the absence or, preferably, in the presence of a solvent. Solvents which are preferably used are excess carbon tetrahalide, or hydrocarbons, such as toluene, or nitriles, such as acetonitrile. Acetonitrile is particularly preferably used. It is also preferable to use alcohols, for example propanol, butanol or pentanol. The reaction is generally carried out at temperatures of about 50° to 150° C., optionally under pressure.

Process (8) can be carried out also using suitable catalysts. Possible catalysts are as follows.

1. Substances which form free radicals, for example benzoyl peroxide, acetyl peroxide, di-tert.-butyl peroxide, tert.-butyl hydroperoxide and azobisisobutyronitrile. In general, catalytic amounts of the agent which forms free radicals are sufficient, but larger amounts are also not harmful.

2. Metal salts in the presence of organic amines. Examples of possible metal salts are copper salts and iron salts, such as copper (I) chloride, copper (II) chloride, iron (II) sulphate and iron (III) chloride. Examples of possible amines are pyrrolidine, piperidine, n-butylamine, cyclohexylamine, triethylamine and dimethylamine. They can also be employed in the form of their salts, for example the hydrochlorides. Catalytic amounts of the catalysts are likewise sufficient for the reaction. Larger amounts accelerate the reaction.

3. The reaction can also be carried out by irradiation with UV light or γ-rays.

However, it should be noted that for compounds of the general formula (VI) in which X represents H only the catalysts listed under 2 are possible.

Compounds of the formula (IX) are known and they can be obtained by known methods (see, for example, U.S. Pat. No. 2,795,617). They are obtained by reacting compounds of the formula (V) with diketene.

As already mentioned, the halogenovinyl-γ-butyrolactones which can be prepared according to the invention are used as intermediates for the preparation of insecticidal active compounds.

The preparation of these active compounds is illustrated by the following equation:

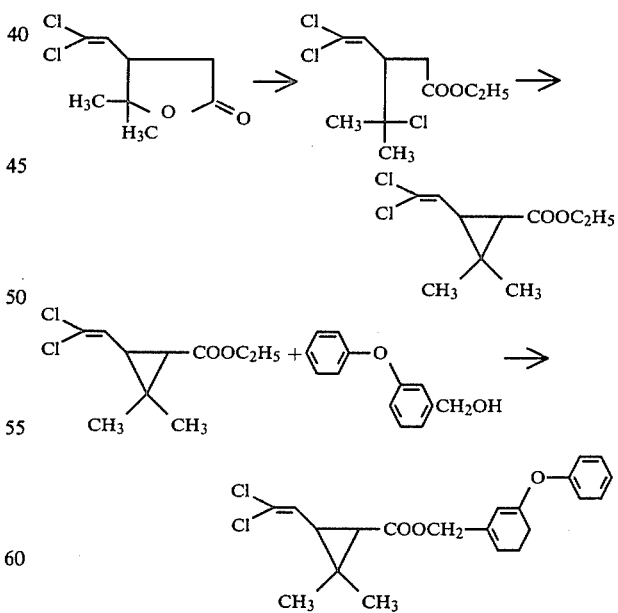

The 2,2-dimethyl-3-(2',2'-dichlorovinyl)-cyclopropanecarboxylic acid m-phenoxybenzyl ester thus obtained is a known insecticidal active compound (see German Offenlegungsschrift (German Published Specification) No. 2 326 077).

The examples which follow illustrate the process according to the invention without indicating a restriction with regard to the extent of its applicability:

Process (1): Preparation of a γ-butyrolactone by deacetylation of a 2-acetyl-γ-butyrolactone

EXAMPLE 1

25.1 g (0.1 mol) of 2-acetyl-3-(2',2'-dichlorovinyl)-4-methyl-γ-valerolactone were suspended in 250 ml of 10% strength sodium hydroxide solution, and 20 g of bromine were then added dropwise at 0°–10° C. After the dropwise addition had ended, excess hypobromite was destroyed with aqueous sodium bisulphite solution and the solution was adjusted to pH 1 with 25% strength sulphuric acid. The reaction product was subjected to filtration, drying and distillation under reduced pressure. 3-(2',2'-Dichlorovinyl)-4-methyl-γ-valerolactone distilled at 160°–170° C./25 mm Hg. The yield was 17.3 g (86% of theory), melting point 108° C.

EXAMPLE 2

34 g (0.1 mol) of 2-acetyl-3-(2',2'-dibromovinyl)-4-methyl-γ-valerolactone were suspended in 250 ml of 10% strength sodium hydroxide solution at 0° C., and 20 g of bromine were then added dropwise at 0°–5° C. After the dropwise addition had ended, excess hypobromite was destroyed with aqueous sodium bisulphite solution and the solution was adjusted to pH 1 with 25% strength sulphuric acid. The solution was then concentrated by distilling off the water. The 3-(2',2'-dibromovinyl)-4-methyl-γ-valerolactone was filtered off, washed with water and dried in air. Melting point 115°–116° C.

EXAMPLE 3

26.4 g (0.1 mol) of 2-acetyl-3-(2',2'-dichlorovinyl)-4-ethyl-γ-valerolactone were dissolved in 100 ml of dioxane. Technical grade hypochlorite solution was then added dropwise at 20–30° C. in an amount such that a total of 0.5 mol of hypochlorite had been added. The mixture was heated to the boil for a further 3–4 hours, any hypochlorite still present was destroyed with sodium bisulphite solution and the mixture was adjusted to pH 1 with 25% strength sulphuric acid. It was then extracted with methylene chloride and the organic phase was subjected to fractional distillation. 16.7 g (75% of theory) of 3-(2',2'-dichlorovinyl)-4-ethyl-γ-valerolactone of boiling point 160°–165° C./20 mm Hg were obtained. Refractive index: $n_D^{20}$:1.5012.

Process (4): Preparation of a 2-acetyl-γ-butyrolactone by splitting off hydrogen halide from acetoacetates of the formula (III).

EXAMPLE 4

A solution of 23 g of sodium in 1,000 ml of ethanol was added dropwise to 162 g (0.5 mol) of the acetoacetate of 2-methyl-3,5,5,5-tetrachloropentan-2-ol at room temperature. The mixture was subsequently stirred at room temperature for 4 hours. It was then heated to the boil for a further 4 hours. After cooling the mixture, the sodium chloride which had formed was filtered off and the ethanol solution was concentrated somewhat, ice-water was added and the mixture was rendered acid. It was extracted with methylene chloride, the methylene chloride solution was dried with sodium sulphate and the solvent was distilled off. The 2-acetyl-3-(2',2'-dichlorovinyl)-4-methyl-γ-valerolactone formed was sufficiently pure to be employed directly as described in Example 1. It distilled at boiling point 135°–145° C./0.7 mm Hg.

EXAMPLE 5

Analogously to Example 4, 2-acetyl-3-(2',2'-dichlorovinyl)-4-ethyl-γ-valerolactone was obtained from the acetoacetate of 3-methyl-4,6,6,6-tetrachlorohexan-3-ol.

EXAMPLE 6

A solution of 23 g of sodium in 1,000 ml of ethanol was added dropwise to 251 g (0.5 mol) of the acetoacetate of 2-methyl-3,5,5,5-tetrabromopentan-2-ol at 0° C. and the mixture was subsequently stirred at 0° C. for 4 hours, then allowed to come to room temperature and concentrated somewhat under reduced pressure. Working up was carried out as in Example 4. 125 g of 2-acetyl-3-(2',2'-dibromovinyl)-4-methyl-γ-valerolactone were obtained, which was processed as described in Example 2.

EXAMPLE 7

112 g of 50% strength KOH were added dropwise at room temperature to 162 g (0.5 mol) of the acetoacetate of 2-methyl-3,5,5,5-tetrachloropentan-2-ol in 200 ml of toluene and 5 g of tetrabutylammonium bromide. The mixture was then heated to 80° C. for a further 1–2 hours. After cooling the mixture, the aqueous phase was rendered strongly acid and the salts which had precipitated were dissolved with water. The organic phase was then separated off and dried with sodium sulphate and the solvent was stripped off under reduced pressure. 105 g of 2-acetyl-3-(2',2'-dichlorovinyl)-4-methyl-γ-valerolactone were obtained.

Process (6)(a): Reaction of the alcohols of the general formula (IV) with diketene.

EXAMPLE 8

85 g of freshly distilled diketene were added dropwise to 240 g of 2-methyl-3,5,5,5-tetrachloro-pentan-2-ol and 3 ml of triethylamine at 50° C., while stirring. During this addition, the temperature rose to about 120° C. After cooling, the mixture was subjected to incipient distillation at 60°–70° C. under a water-pump vacuum. The residue consisted of fairly pure 2-methyl-3,5,5,5-tetrachloropentan-2-ol acetoacetate. $n_D^{20}$:1.4921.

The structure was confirmed by the nuclear magnetic resonance spectrum (in CDCl$_3$).

δ(ppm)=1.6 (d, 6 protons, CH$_3$, CH$_3$), 2.25 (s, 3 protons, CH$_3$), 2.8–3.6 (m, 2 protons, CH$_2$CCl$_3$); 3.4 (s, 2 protons, CH$_2$CO); and 4.5–4.7 (m, 1 proton, CHCl).

An OH band was no longer present in the IR spectrum.

EXAMPLE 9

Analogously to Example 8, 3-methyl-4,6,6,6-tetrachlorohexan-3-ol and diketene gave the corresponding acetoacetate.

Process (6)(b): (i) Preparation of the acetoacetate of isoprene-alcohol.

EXAMPLE 10

84 g of freshly distilled diketene were added dropwise to 86 g of isoprene-alcohol (2-methyl-3-buten-2-ol) and 1 ml of triethylamine. During this procedure, the temperature rose to about 130° C. After cooling, the reaction mixture was distilled under reduced pressure. 148 g (87% of theory) of 2-methyl-3-butenyl-2-acetoacetate of boiling point 95°–100° C./15 mm Hg were obtained. $n_D^{20}$:1.4381.

(ii) Addition reactions with compounds of the general formula (VI)

EXAMPLE 11

A mixture of 85 g of 2-methyl-3-butenyl-2-acetoacetate, 166 g of carbon tetrabromide and 10 g of benzoyl peroxide was heated to 100° for 3 hours. After cooling, the mixture was taken up in methylene chloride, the methylene chloride solution was washed with bicarbonate solution and then with water, the organic phase was separated off and dried with sodium sulphate and the solvent was distilled off under reduced pressure. The acetoacetate of 2-methyl-3,5,5,5-tetrabromo-pentan-2-ol which remained could be employed directly as described in Example 6.

EXAMPLE 12

A mixture of 85 g of 2-methyl-3-buten-2-ol acetoacetate, 1,000 g of carbon tetrachloride and 20 g of water-containing benzoyl peroxide was heated to the boil for 5 hours using a water separator. After cooling, the mixture was washed with 1 N NaOH and excess CCl$_4$ was then distilled off under reduced pressure. The residue was distilled under a high vacuum. The 2-methyl-3,5,5,5-tetrachloro-pentyl-2-acetoacetate so formed boiled at 120°–130° C./0.4 mm Hg.

Process (8): Preparation of alcohols of the general formula (IV).

EXAMPLE 13

430 g (5 moles) of 2-methyl-3-buten-3-ol, 2,500 ml of CCl$_4$ and 80 g of water-containing benzoyl peroxide were heated to the boil for 10 hours using a water separator. After cooling, the mixture was subjected to fractional distillation. 971 g (81% of theory) of 2-methyl-3,5,5,5-tetrachloropentan-2-ol of boiling point 75°–85° C./0.1 mm Hg were obtained. $n_D^{20}$:1.4975.

EXAMPLE 14

Analogously to Example 13, 3-methyl-4,6,6,6-tetrachlorohexan-3-ol of boiling point 90°–98° C./0.4 mm Hg was obtained in 80% yield from 3-methyl-1-penten-3-ol.

EXAMPLE 15

86 g (1 mole) of 2-methyl-3-buten-2-ol, 420 g of difluorodibromomethane and 20 g of benzoyl peroxide (in diethyl phthalate) were heated to 85° C. for 4 hours in a 0.7 liter autoclave. After cooling down, the mixture was subjected to fractional distillation. 285 g (96.5% of theory) of 2-methyl-3,5-dibromo-5,5-difluoro-pentan-2-ol of boiling point 52° C./0.35 mm Hg were obtained. Refractive index $n_D^{20}$:1.4747.

It will be appreciated that the instant specification and examples are set forth by way of illustration and not limitation, and that various modifications and changes may be made without departing from the spirit and scope of the present invention.

What we claim is:

1. A process for the preparation of a halogenovinyl-γ-butyrolactone of the formula

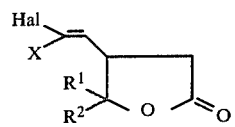

in which
Hal is F, Cl or Br,
X is H, F, Cl or Br and
$R^1$ and $R^2$ each independently is $C_{1-4}$-alkyl or $R^1$ and $R^2$, together with the adjacent C atom, form a cycloaliphatic ring with up to 7 C atoms, comprising deacetylating an acetyl lactone of the formula

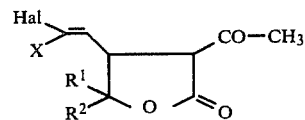

with a hypohalite at a temperature from −20° to 100° C.

2. A process according to claim 1, in which $R^1$ and $R^2$ both are methyl.

3. A process according to claim 1, in which the hypohalite is in aqueous solution.

4. A process according to claim 3, in which the hypohalite is an alkali metal or alkaline earth metal hypohalite.

5. A process according to claim 4, in which the hypohalite is a sodium, potassium or calcium hypochlorite or hypobromite.

6. A process according to claim 1, in which the reaction is effected in the presence of an alcohol or ether as a diluent.

7. A process according to claim 1, wherein the acetyl lactone is produced by reacting a compound of the formula

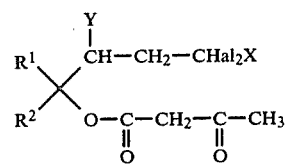

with a base, thereby to split off two mols of hydrogen halide, wherein Y represents chlorine or bromine.

8. A process according to claim 7, wherein the compound of the formula

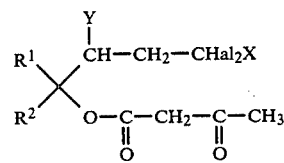

is produced by reacting an alcohol of the formula

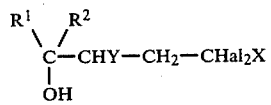

with diketene.

9. A process according to claim 7, where the compound of the formula

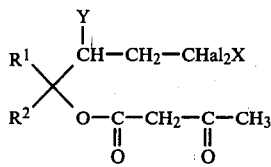

is produced by reacting an alcohol of the formula

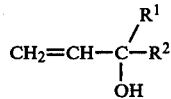

with diketene to produce an acetoacetate of the formula

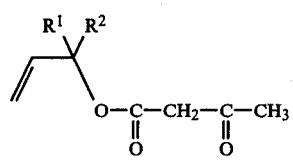

and the acetoacetate is reacted with a compound of the formula

10. A process according to claim 8, wherein the compound of the formula

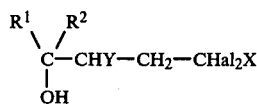

is produced by reacting a compound of the formula

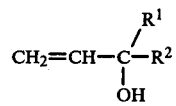

with a compound of the formula

such compound containing at most two fluorine atoms, and at most one fluorine atom if X is hydrogen.

11. A process according to claim 5, including the preliminary steps of reacting a compound of the formula

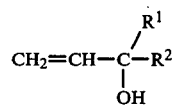

with a compound of the formula

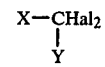

such compound containing at most two fluorine atoms, and at most one fluorine atom if X is hydrogen, reacting the product with diketene to produce the compound of the formula

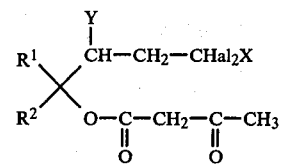

and reacting that compound with a base thereby to split off hydrogen halide and produce the acetyl lactone, deacetylation of the acetyl lactone being effected at from 20° to 100° C. in the presence of methanol, ethanol, dioxane or tetrahydrofuran, and after deacetylation the reaction mixture is acidified.

12. A process according to claim 5, including the preliminary steps of reacting an alcohol of the formula

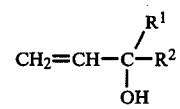

with diketene to produce an acetoacetate of the formula

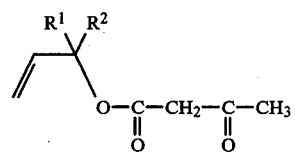

reacting the acetoacetate with a compound of the formula

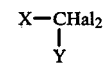

to produce a compound of the formula

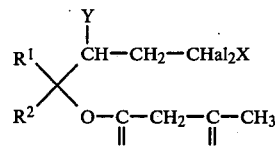

and reacting that compound with a base thereby to split off hydrogen halide and produce the acetyl lactone, deacetylation of the acetyl lactone being effected at from 20° to 100° C. in the presence of methanol, ethanol, dioxane or tetrahydrofuran, and after deacetylation the reaction mixture being acidified.

13. An acetyl lactone of the formula

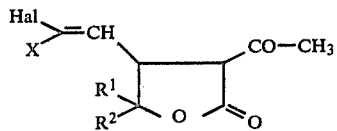

in which
Hal is F, Cl or Br,
X is H, F, Cl or Br and
$R^1$ and $R^2$ each independently is $C_{1-4}$-alkyl or $R^1$ and $R^2$ together with the adjacent C atom, form a cycloaliphatic ring with up to 7 C atoms.

14. A process for producing an acetyl lactone according to claim 13, comprising reacting a compound of the formula

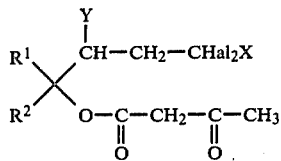

with a base, thereby to split off two mols of hydrogen halide, wherein Y represents chlorine or bromine.

* * * * *